(12) United States Patent
Kataoka et al.

(10) Patent No.: US 7,252,912 B2
(45) Date of Patent: Aug. 7, 2007

(54) POLYMER COMPOSITE

(75) Inventors: Kazunori Kataoka, 17-22, Kamisaginomiya 5-chome, Nakano-ku, Tokyo (JP) 165-0031; Akihiro Hirano, Ichikawa (JP); Takeshi Ikeya, Inba-gun (JP); Toru Shibuya, Inba-gun (JP)

(73) Assignees: Kazunori Kataoka, Nakano-ku, Tokyo (JP); Toyo Gosei Co., Ltd., Ichikawa-shi, Chiba (JP)

( * ) Notice: Subject to any disclaimer, the term of this patent is extended or adjusted under 35 U.S.C. 154(b) by 0 days.

(21) Appl. No.: 11/094,076

(22) Filed: Mar. 29, 2005

(65) Prior Publication Data

US 2006/0222876 A1    Oct. 5, 2006

(30) Foreign Application Priority Data

Mar. 29, 2004   (JP)   ............... 2004-096854

(51) Int. Cl.
*G03F 7/012*  (2006.01)
*G03F 7/008*  (2006.01)
*G03F 7/038*  (2006.01)
*G03F 7/11*   (2006.01)
*G03F 7/085*  (2006.01)

(52) U.S. Cl. .............. 430/17; 430/167; 430/271.1; 430/954; 428/420

(58) Field of Classification Search .......... 430/167, 430/17, 271.1, 954; 428/420
See application file for complete search history.

(56) References Cited

U.S. PATENT DOCUMENTS 4,218,513 A * 8/1980 Williams et al. ............ 428/419
4,491,629 A * 1/1985 Koike et al. ................ 430/176
4,596,755 A * 6/1986 Koike et al. ................ 430/196
4,969,998 A * 11/1990 Henn ......................... 210/490
6,156,478 A * 12/2000 Liu et al. .................. 430/270.1

FOREIGN PATENT DOCUMENTS

| JP | 07-113773   | 5/1995  |
| JP | 09-127041   | 5/1997  |
| JP | 10-310769   | 11/1998 |
| JP | 2003-292477 | 10/2003 |

OTHER PUBLICATIONS

Nishikawa, Y et al., Contruction of Artificial Extracellular Matrix by Self-Organization of Amphiphilic Polymer, Polymer Processing, 2001, pp. 10-15 vol. 50. No. 1.

* cited by examiner

*Primary Examiner*—Richard L. Schilling
(74) *Attorney, Agent, or Firm*—Brian A. Gomez; Gomez International Patent Office, LLC

(57) ABSTRACT

A polymer composite comprises a base material, and a polymer membrane provided on at least a part of the base material, the polymer membrane having at least hydrophilicity, and the polymer composite is used in a state exposed to water or a water-based solvent. The polymer membrane is a resin film formed by photo-crosslinking a photosensitive resin composition consisting essentially of a water-soluble polymer, and during crosslinking of the photosensitive resin composition, some of photosensitive groups of the photosensitive resin composition are bound to amino groups fixed to the surface of the base material, whereby the resin film is fixed to the base material.

9 Claims, 2 Drawing Sheets

COMPARATIVE EXAMPLE 4     BEFORE DIPPING

COMPARATIVE EXAMPLE 4     DIPPING FOR 75 HOURS

COMPARATIVE EXAMPLE 4     DIPPING FOR 236 HOURS

EXAMPLE 4     BEFORE DIPPING

EXAMPLE 4     DIPPING FOR 75 HOURS

EXAMPLE 4     DIPPING FOR 236 HOURS

POLYMER COMPOSITE

CROSS REFERENCE TO RELATED APPLICATION

The entire disclosure of Japanese Patent Application No. 2004-096854 filed on Mar. 29, 2004, including specification, claims, drawings and summary, is incorporated herein by reference in its entirety.

BACKGROUND OF THE INVENTION

1. Field of the Invention

This invention relates to a polymer composite comprising a hydrophilic polymer membrane provided on a base material, the polymer composite being used exposed to water or a water-based solvent, and uses of the polymer composite.

2. Description of the Prior Art

Polymer composites, which have a hydrophilic polymer membrane provided on a base material and find use as exposed to water or a water-based solvent, have hitherto been used as components of biosensors (see Japanese Patent Application Laid-Open No. 09-127041). Among them are polymer composites which are produced by coating an aqueous solution of a mixture of a compound derived from a polyvinyl acetate saponification product, glutaraldehyde as a thermal crosslinking agent, and a physiologically active substance on a base material, and crosslinking these materials by heat. If such polymer composites use the physiologically active substance which does not accept high temperatures, they pose a process-related problem that crosslinking needs to be performed at a low temperature over a long period of time of the order of 24 hours.

A polymer composite, which has a polymer membrane comprising a PVA-SBQ (polyvinyl alcohol having a stilbazolium group) solution photo-crosslinked on a substrate, is known for use in a biosensor (see Japanese Patent Application Laid-Open No. 07-113773). However, this polymer composite involves the problem that when it is exposed to water or a water-based solvent, the polymer membrane peels off the substrate in a short time, or the polymer membrane collapses because of cracks, etc. The same problem is true of the polymer composite which uses a photo-crosslinking agent as described in the aforementioned Japanese Patent Application Laid-Open No. 09-127041.

On the other hand, a base material for cell culture is used exposed to a water-based solvent. A known cell culture base material has a polymer pattern carried on a base material, the polymer pattern comprising a polymer precipitated by using, as templates, water droplets which have gathered on the surface of a solution during evaporation of an organic solvent from a solution of a hydrophobic polymer in the organic solvent under high humidity conditions (see Polymer Processing, Vol. 50, No. 1 (2001), P. 10-15). However, this polymer pattern is hydrophobic, and thus cannot suppress the nonspecific adsorption of an adhesive protein. As a result, the problem arises that cells other than the desired cells adhere to the polymer pattern, rendering a precision culture impossible.

SUMMARY OF THE INVENTION

The present invention has been accomplished in the light of the above-mentioned problems. It is an object of the invention to provide a polymer composite which, even when used in a state exposed to water or a water-based solvent, can maintain a stable structure for a long term, and which can be preferably used as a base material for cell culture or as a material for a biosensor.

A first aspect of the present invention for attaining the above object is a polymer composite comprising a base material and a polymer membrane provided on at least a part of the base material, the polymer membrane having at least hydrophilicity, the polymer composite being used in a state exposed to, water or a water-based solvent, wherein the polymer membrane is a resin film formed by photo-crosslinking a photosensitive resin composition consisting essentially of a water-soluble polymer, and during crosslinking of the photosensitive resin composition, some of photosensitive groups of the photosensitive resin composition are bound to amino groups fixed to the surface of the base material, whereby the resin film is fixed to the-base material.

A second aspect of the polymer composite of the present invention according to the first aspect is characterized in that the resin film is formed by exposing to light the entire surface of the photosensitive resin composition coated on the base material to crosslink the photosensitive resin composition.

A third aspect of the polymer composite of the present invention according to the first aspect is characterized in that the resin film is provided on the part of the base material by pattern exposure and development of the photosensitive resin composition coated on the base material to remove unexposed areas.

A fourth aspect of the polymer composite of the present invention according to the third aspect is characterized in that after the development, traces of the photosensitive resin composition on the surface of the base material in the unexposed areas are removed.

A fifth aspect of the polymer composite of the present invention according to the fourth aspect is characterized in that the amino groups on the surface of the base material in the unexposed areas are removed.

A sixth aspect of the polymer composite of the present invention according to any one of the first to fifth aspects is characterized in that the photosensitive resin composition is (a) a composition containing a water-soluble polymer having azido groups as the photosensitive groups, (b) a composition containing a water-soluble photo-crosslinking agent having azido groups as the photosensitive groups, and a water-soluble polymer having no photosensitive groups, or (c) a composition containing a water-soluble polymer having azido groups as the photosensitive groups, a water-soluble polymer having no photosensitive groups, and a water-soluble photo-crosslinking agent having azido groups as the photosensitive groups.

A seventh aspect of the polymer composite of the present invention according to the sixth aspect is characterized in that the photosensitive groups have a structure of the following formula (1) or formula (2):

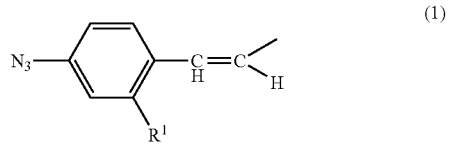

-continued

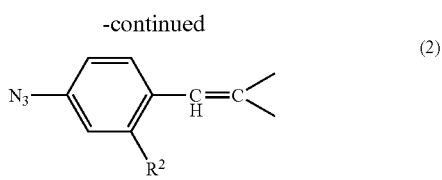
(2)

where $R^1$ and $R^2$ each represent a hydrogen atom, a sulfonic group, or a sulfonate group.

An eighth aspect of the polymer composite of the present invention according to any one of the first to seventh aspects is characterized in that the water-based solvent is at least one member selected from the group consisting of a physiological buffer solution, a protein-containing aqueous solution, a DNA-containing aqueous solution, an RNA-containing aqueous solution, a sugar-containing aqueous solution, a liquid culture medium, and a cell suspension.

A ninth aspect of the polymer composite of the present invention according to any one of the first to eighth aspects is characterized in that the polymer composite is a matrix material for a biosensor, or a base material for cell culture.

The present invention can provide a water-soluble polymer composite which is stable for a long period of time when exposed to water or a water-based solvent. This polymer composite can be preferably used as a gelling agent or a surface modifier by a water-soluble polymer which is expected to be used while exposed to water or a water-based solvent, concretely, a matrix for a biosensor or a base material for cell culture. Thus, the polymer composite produces the effect of contributing to the construction of a device in the field of life science or in the environmental field.

BRIEF DESCRIPTION OF THE DRAWINGS

For a more complete understanding of the present invention and the advantages thereof, reference is now made to the following descriptions in conjunction with the accompanying drawings.

DESCRIPTION OF THE PREFERRED EMBODIMENTS

Figure 1A:
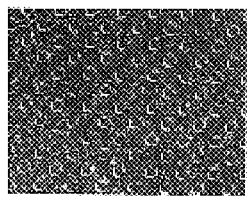
FIG. 1A to 1F presents views showing an example of the status of the polymer composite after stability evaluation tests.
Figure 1B:
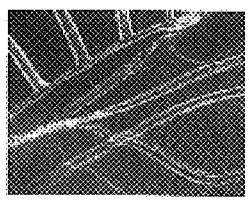
Figure 1C:
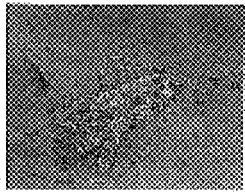
Figure 1D:
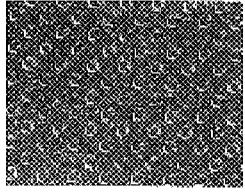
Figure 1E:
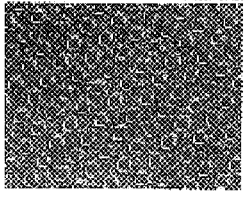
Figure 1F:
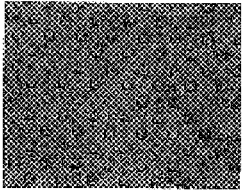

The present invention will now be described in detail based on the embodiments offered below.

The polymer composite of the present invention comprises a base material and a polymer membrane provided on at least a part of the base material, the polymer membrane having at least hydrophilicity, the polymer composite being used in a state exposed to water or a water-based solvent. The polymer membrane provided on at least the part of the base material is a resin film formed by photo-crosslinking a photosensitive resin composition consisting essentially of a water-soluble polymer. During crosslinking of the photosensitive resin composition, some of photosensitive groups of the photosensitive resin composition are bound to amino groups fixed to the surface of the base material, whereby the resin film is fixed to the base material.

The photosensitive resin composition used in the present invention is a composition containing a water-soluble polymer as a main component, and having photosensitive groups. However, the photosensitive resin composition may be a composition containing a water-soluble polymer having photosensitive groups, or may be a composition containing a water-soluble photo-crosslinking agent, namely, a compound having a photosensitive group, and a water-soluble polymer having no photosensitive group. Alternatively, the photosensitive resin composition may be a composition containing a water-soluble polymer having photosensitive groups, a water-soluble polymer having no photosensitive groups, and a water-soluble photo-crosslinking agent. The content of the water-soluble polymer is preferably 70 wt. % or more, more preferably 85 wt. % or more, based on the solids content in the photosensitive resin composition.

No restriction is imposed on the photosensitive groups contained in the photosensitive resin composition for forming the resin film. The photosensitive groups may be publicly known photosensitive groups, but are particularly preferably photosensitive groups having azido groups. The reason is that azido groups, which are photosensitive, and amino groups fixed to the surface of the base material together form stable covalent bonds upon irradiation with light, and can thus maintain the polymer composite more stably.

Particularly preferably, the photosensitive groups having azido groups have the structure represented by the aforementioned formula (1) or (2). The formula (1) shows a monovalent group, and the formula (2) shows a divalent group. In either formula, the sulfonate group is represented by —$SO_3M$, in which M is exemplified by an alkaline metal, such as sodium or potassium. The photosensitive group may be directly bound to the water-soluble photo-crosslinking agent or to the water-soluble polymer, or may be bound thereto via a spacer such as alkylene or via an amide bond.

A publicly known component for the photosensitive resin composition can be used as the water-soluble polymer. Examples are a polyvinyl acetate saponification product, polyvinyl pyrrolidone, poly(meth)acrylamide-diaceton (meth)acrylamide copolymer, poly-N-vinylformamide, and poly-N-vinylacetamide. Of these polymers, polyvinyl acetate saponification product can be used preferably. The degree of polymerization and the degree of saponification of the polyvinyl acetate saponification product are not limited, but that having an average degree of polymerization of 200 to 5000 and a degree of saponification of 60 to 100% can be used preferably. If the average degree of polymerization is lower than 200, it is difficult to obtain sufficient sensitivity. If the average degree of polymerization is higher than 5000, the viscosity of the photosensitive resin composition is so high that poor coating properties tend to occur. A lowered concentration for decreasing the viscosity poses difficulty in obtaining the desired coating thickness. A degree of saponification of less than 60% makes it difficult to obtain sufficient water-solubility and water developability.

To obtain the water-soluble polymer having photosensitive groups, it is recommendable, for example, to react a compound having a photosensitive group (a photosensitive group unit) with the water-soluble polymer. Examples of the compound having a photosensitive group for introducing the photosensitive group into the water-soluble polymer are photosensitive group units described-in Japanese Patent Application Laid-Open No. 2003-292477, such as 3-(4-azidophenyl)-N-(4,4'-dimethoxybutyl)-2-phenylcarbonylamino-prop-2-enamide) (hereinafter referred to as "photosensitive compound 1"), 2-(3-(4-azidophenyl)prop-2- enoylamino)-N-(4,4'-dimethoxybutyl)-3-(3-pyridyl)prop-2-enamide) (hereinafter referred to as "photosensitive compound 2"), and 3-(4-azidophenyl)-N-(4,4'-dimethoxybutyl)-2-[(3-pyridyl)carbonylamino]prop-2-enamide) (hereinafter referred to as "photosensitive compound 3"), and photosensitive group units described in Japanese Patent No. 3163036, such as 3-(2-dimethoxybutyl)-(4-azidobenzylidene-2-sulfonic acid sodium)rhodanine (hereinafter referred to as "photosensitive compound 4"), and 3-(2-dimethoxyethyl)-(4-azidobenzylidene-2-sulfonic acid sodium)rhodanine. The compounds in Japanese Patent Application Laid-Open No. 2003-292477 and Japanese Patent No. 3163036 are used mainly as resist materials, and are not intended to be used under conditions exposed to water or a water-based solvent for a long period of time.

The water-soluble photo-crosslinking agent is not limited, and may be any one which has a photosensitive group. However, one having an azido group as a photosensitive group, as described above, is preferred. For example, there can be named 4,4'-diazidostilbene-2,2'-disulfonic acid (hereinafter referred to as "photosensitive compound 5"), 4,4'-diazidobenzalacetophenone-2-sulfonic acid, 4,4'-diazidostilbene-α-carboxylic acid, and alkaline metal salts, ammonium salts, and organic amine salts of them.

The photosensitive resin composition is preferably in the state of a solution. A solvent for the photosensitive resin composition is not limited, as long as it can dissolve the components contained in the composition. Water or a mixed solution of water and an organic solvent compatible with water can be used. Nonrestrictive examples of the organic solvent compatible with water are ketones such as acetone, lower alcohols such as methanol, acetonitrile, and tetrahydrofuran. The concentration of the solids is preferably 10 wt. % or less.

Moreover, additives whose amounts do not impair the photocurability of the photosensitive resin composition may be added to the photosensitive resin composition. For example, it is possible to add substances necessary when using the polymer composite of the present invention for application to sensors, enzymes such as glucose oxidase, antibodies such as immunoglobulin-G (IgG), DNA and RNA used as probes, proteins, and polysaccharides.

The base material, on which the resin film formed by photo-crosslinking of the photosensitive resin composition is provided, needs to have amino groups on the surface. The amino groups present on the surface of the base material are not limited, if they can exist stably. As the method of imparting amino groups to the surface of the base material, it is possible to use a publicly known method, such as plasma processing in ammonia or under an organic base atmosphere, surface coating with a polymer material having an amino group, modification of the surface of the base material with a surface modifier, or the use of the base material which itself has an amino group exposed at the surface. The material for imparting amino groups to the surface of the base material is not limited, but preferably poly-L-lysine can be used.

The shape of and the material for the base material are not limited. Examples of the material for the base material are, but not limited to, glass, thermoplastic resins, thermosetting resins, silicon, diamond, metals, and ceramics. The shape of the base material includes, for example, a plate form, a plate form with a curved surface, a fibrous form, a form having a microporous surface structure, a capillary form, and a tubular form, but these forms are not limitative. Preferably, glass can be used as the material, and the plate form can be used as the shape. This is because such a material and such a shape can be used preferably in preparing a pattern structure through the aid of a mask.

The polymer composite of the present invention can be obtained by the step of coating the photosensitive resin composition on the base material to form a coating of the photosensitive resin composition; the step of exposing to light the coating of the photosensitive resin composition to form a polymer membrane; and, if desired, the step of performing development with water or a water-based developer to form a polymer membrane.

The thickness of the photosensitive resin composition coated on the base material is not limited, if the thickness allows coating. However, the preferred coating thickness is 5 nm to 5 μm. If the coating thickness is less than 5 nm, it is difficult to make sure that the coating is uniform. If the coating thickness exceeds 5 μm, it is necessary to increase the viscosity of the photosensitive resin solution used, thus tending to pose the process problem of deteriorating coating properties.

After the photosensitive resin composition is coated on the base material, the resulting coating may be heat-treated; if desired. The heat-treatment is optional, and does not require particular conditions. Usually, however, the heat-treatment is performed for 1 minute to 10 hours at 30 to 150° C., preferably, for 3 minutes to 1 hour at 35 to 120° C.

The entire surface of the photosensitive resin composition coated on the base material may be exposed to light, or a desired pattern portion of the photosensitive resin composition may be exposed to light. Upon pattern exposure, the unexposed areas are removed by post-exposure development, whereby a polymer composite having an arbitrary patterned form can be obtained.

For pattern exposure, exposure to light may be performed through a mask. The mask for forming an arbitrary pattern can be a mask having the desired pattern cut out, or a mask composed of only the desired pattern. The mask may be designed such that if the photosensitive resin is of a negative type, the site to be cured is transparent to light. The mask is preferably of a type which minimizes passage of light used during exposure.

The light source for exposure is not limited, if it can photosensitize the photosensitive group used. For example, X-rays, electron rays, an excimer laser ($F_2$, ArF, or KrF laser), and a high pressure mercury lamp can be used as the light source. Of these light sources, a wavelength with a high photosensitization efficiency can be used as desired. The exposure energy can be set, as appropriate, in accordance with the structure of the photosensitive group and the energy of the light source used. Usually, the exposure energy is 0.1 mJ/cm to 10 $J/cm^2$, preferably 1 $mJ/cm^2$ to 1 $J/cm^2$.

In the case of exposure of the entire surface to light, it is permissible, if desired, to carry out heating, followed by washing with water. The heat-treatment is optional, and does not require any particular conditions. Usually, however, the heat-treatment is performed for 1 minute to 10 hours at 30 to 150° C., preferably, for 3 minutes to 1 hour at 35 to 120° C. Furthermore, after the physical properties of the coating of the photosensitive resin composition are changed by pattern exposure, the exposed coating is heated if desired, and then developed. The heat-treatment is optional, and does not require particular conditions. Usually, however, the heat-treatment is performed for 1 minute to 10 hours at 30 to 150° C., preferably, for 3 minutes to 1 hour at 35 to 120° C.

The developer for development is not limited, if it gives a sufficient difference in solvency between the unexposed areas and the exposed areas. Water or a mixed solution of water and an organic solvent compatible with water can be used as the solvent which can dissolve the unexposed areas of the water-soluble polymer. Nonrestrictive examples of the organic solvent compatible with water are ketones such as acetone, lower alcohols such as methanol, acetonitrile, and tetrahydrofuran. If any of these solvents is used, a satisfactory pattern without undeveloped regions can be prepared preferably. The developer may be a mixed solution as described above, and its concentration is not limited, as long as the concentration is enough to dissolve the unexposed areas. If the developer is a mixed solution of water and methanol, the concentration of the methanol can take any value less than 100 wt. %.

The development can be performed by dipping in the developer the exposed material to be treated, or coating the developer on the exposed material to be treated, or spraying the developer over the exposed material to be treated. After pattern formation by development, a rinsing step, a drying step, etc. can be added, where necessary.

In the case of the patterned polymer composite, even after the photosensitive resin composition in the unexposed areas is removed by development, the photosensitive resin composition corresponding to several molecular layers may remain on the base material as a result of physical adsorption. Thus, traces of the photosensitive resin composition remaining in the unexposed areas after development, namely, an extremely thin layer of the photosensitive resin composition, can be removed, where necessary, whereafter the polymer composite can be used. The method of removing the remaining layer is not limited, but ashing by irradiation with plasma, chemical etching, etc. can be named as nonrestrictive examples. Ashing by oxygen plasma, in particular, can be preferably used. By removing the traces of the photosensitive resin composition, influences of the photosensitive resin composition can be excluded. The influences of the photosensitive resin composition include, for example, the suppression of protein adsorption and the suppression of cell adhesion. In using the polymer composite, obtained in the present invention, as a precision cell culture base material for pattern culture, for example, it is necessary that cell adhesion does not occur on the polymer membrane, but cell adhesion takes place at the site where the base material is exposed to the outside, namely, the site corresponding to the unexposed areas. To use a structure formed by the polymer composite of the present invention as a base material for cell culture, therefore, it is not preferred for the suppressions of adsorption and adhesion to occur even in the unexposed areas after development which require cell adhesion. Thus, the remaining traces of the photosensitive resin composition should preferably be removed.

Not only the traces of the photosensitive resin composition in the unexposed areas, but also the amino groups on the surface of the base material in the unexposed areas can be removed, whereafter the so treated polymer composite of the present invention can be used. The removal of the amino groups on the surface of the base material can be performed by the same method as that for the removal of the traces of the photosensitive resin composition. Cell adhesion to the site of outward exposure of the base material, corresponding to the unexposed areas (areas unexposed to light), is presumed to be mainly induced by the fact that hydrophobicity is stronger in the site of outward exposure than in the polymer membrane present in the surroundings of the unexposed areas, and the stronger hydrophobicity causes the adsorption of an adhesive protein such as fibronectin, which in turn triggers cell adhesion. Hence, the amino groups on the surface of the base material, which are cationic groups, are removed, whereby it becomes possible to suppress nonspecific biological reactions due to the adsorption of various proteins under an electrostatic interaction, or the adsorption of cells having a negatively charged surface. If only the water-soluble polymer is removed, and the amino groups on the surface of the base material, especially, poly-L-lysine is allowed to remain, then it is possible to obtain a cell culture base material which can impart specific stimuli to particular cells on account of the poly-L-lysine having the amino group.

The polymer composite of the present invention can be used preferably, with its structure being maintained stably for a long period of time, for example, for a day or more, while being exposed to water or a water-based solvent. The principle, on which the polymer composite can maintain its structure stably for a long period of time during exposure to water or a water-based solvent, has not been elucidated. However, it is presumed that some of the amino groups present on the surface of the base material, and some of the photosensitive groups present in the photosensitive resin composition undergo a chemical reaction when irradiated with light, forming a covalent bond. For example, when there is used the photosensitive resin composition containing polyvinyl acetate saponification product incorporating azido groups as the photosensitive groups, the azido groups in the polyvinyl acetate saponification product are considered to be mostly consumed for a crosslinking reaction upon irradiation with light. However, some of the azido groups may covalently bind to the surface of the base material at many locations, thereby increasing resistance to peeling due to wetting with water or the water-based solvent. Actually, when the polymer composite was similarly prepared on the base material having no amino groups on the surface, dipping of the polymer composite in water for only a day caused marked peeling of the polymer membrane on the base material. This is proof of the above presumption.

The water-based solvent is not limited, if it is a solution containing water. Its nonrestrictive examples include mixtures of water and organic solvents compatible with water, e.g., ketones such as acetone, lower alcohols such as methanol, acetonitrile, and tetrahydrofuran; buffer solutions such as an aqueous solution of potassium trihydrogenbis(oxalate), an aqueous solution of potassium hydrogenphthalate, an aqueous solution of potassium dihydrogenphosphate and disodium hydrogenphosphate, an aqueous solution of sodium tetraborate, and an aqueous solution of sodium hydrogencarbonate and sodium carbonate; aqueous solutions of inorganic and organic salts, such as sodium chloride, potassium chloride, ammonium chloride, sodium bromide, potassium bromide, and ammonium bromide; aqueous solutions of nonionic surface active agents, such as polyoxyethylene alkyl ether, polyoxyethylene alkylphenol ether, polyoxyethylene monoacyl ester, sorbitan monoacyl ester, polyoxyethylene sorbitan monoester, and fatty acid monoglyceride; aqueous solutions of ionic surface active agents, such as sodium oleate, sodium dodecyl sulfate, sodium dodecylbenzenesulfonate, cholic acid, deoxycholic acid, chenodeoxycholic acid, laurylamine acetate, quaternary ammonium salt, lauryl-p-alanine, alkylbetaine, and alkyl aminopolyoxyethylenesulfate; aqueous solutions of sugars including monosaccharides, oligosaccharides, and polysaccharides, such as allose, altrose, glucose, mannose, gulose, idose, galactose, talose, ribose, arabinose, xylose, lyxose, erythrose, threose, psicose, fructose, sorbose, tagatose, fucose, deoxy sugars, aminosugars, uronic acid, sulfur sugars, alditol, cyclitol, ulose, branched sugars, D-glucose, starch, heparin, and heparan sulfate; aqueous solutions of proteins; aqueous solutions of DNA and RNA; liquid culture media; and mixtures of these. The water-based solvent may contain substances which are not dissolved, but dispersed in water or the water-based solvent. Nonrestrictive examples of such substances are minerals such as clay, fine metal particles such as gold nanoparticles, fine polymer particles such as polystyrene beads and latex particles, animal cells, plant cells, microorganisms, viruses, or mixtures of these.

The temperature at which the polymer composite according to the present invention can be used is not limited, as long as it does not make the resulting structure unstable. However, preferably a temperature of 4 to 80° C. can be used, and especially preferably a temperature of 10 to 60° C. can be used. At a temperature lower than 4° C., water may partly freeze to impair the stability of the polymer composite. At a temperature in excess of 80° C., the photosensitive groups or photo-crosslinking agent bound to the water-soluble polymer may be decomposed, and become unable to retain the structure.

The polymer composite can maintain its structure stably for a long period of time even when used during exposure to water or the water-based solvent. Normally, a structure of such a polymer composite is dissolved or destroyed in a day or so, and thus its long-term stability in water has to be improved by inclusion of a special step. According to the present invention, on the other hand, a polymer composite having stability to water can be obtained by a relatively simple method involving the use of a base material having amino groups on the surface.

Thus, the polymer composite according to the present invention can be used as a matrix at the site of detection in a biosensor. In the case of a biosensor for detecting the concentration of glucose, for example, glucose oxidase capable of reducing glucose to generate hydrogen peroxide is incorporated into the photosensitive resin composition, and this photosensitive resin composition is photo-cured on the detection base material having amino groups. By this procedure, a glucose sensor, which is free from a decrease in output for a long period of time in water or an aqueous solution, can be constructed.

Similarly, a polymer composite containing biotin is formed on the surface of gold having amino groups, for example, with the use of the photosensitive resin composition containing biotin. By this procedure, a surface plasmon resonance (SPR) biosensor capable of detecting actin can be constructed.

In a purification system for activated sludge or the like, the photosensitive resin composition is photo-cured, with useful microorganisms being contained therein, whereby its long-term use for purification can be made without a decrease in the activity of the microorganisms.

Furthermore, a polymer composite is prepared using a culture base material having amino groups. This makes it possible to design arbitrarily a hydrophilic surface, or both a hydrophilic surface and a hydrophobic surface. A polymer composite having such surfaces can be conveniently used in new culture systems, such as those for pattern culture.

The base material for cell culture is a polymer composite formed by using glass having amino groups, or hydrophilicized polystyrene as a base material, and patterning a photosensitive resin composition on the base material so as to have a form such as holes or stripes. This procedure can achieve a cell culture base material in which no cells adhere onto a polymer membrane, and cells adhere only to sites where the base material is exposed to the outside, so that the cells are arranged in a pattern.

EXAMPLES

The present invention will now be described in detail based on the following examples, which in no way limit the present invention:

Example 1

A poly-L-lysine-coated slide glass (a product of Matsunami Glass Ind.,Ltd., hereinafter referred to as "PLL-coated glass") was used as a base material having amino groups on the surface. An aqueous solution of a polyvinyl acetate saponification product incorporating 0.75 mol % of photosensitive compound 2, a photosensitive compound having azido groups, was prepared (the aqueous solution was designated as photosensitive resin composition A; trademark "AWP", Toyo Gosei Co., Ltd.). The photosensitive resin composition A (solids concentration: 5 wt. %) was added dropwise onto the PLL-coated glass, then formed into a film by spin coating (1000 rpm×30 seconds), dried for 10 minutes at 60° C., and then cooled to room temperature. The film thickness obtained was 0.84 µm. This product was exposed to light, throughout its surface, by a high pressure mercury lamp (amount of exposure: 30 mJ/cm$^2$). Then, the exposed product was washed for 1 minute in water at 25° C., and then dried for 10 minutes at 60° C. A polymer composite, which had a polymer membrane formed on the base material upon photo-curing of the photosensitive resin composition, was obtained.

Example 2

A polymer composite having a polymer membrane formed on the base material upon photo-curing was obtained in the same manner as described in Example 1, except that the conditions for spin coating used in Example I were changed from 1000 rpm×30 seconds to 2500 rpm×30 seconds. The film thickness obtained before photo-curing was 0.39 µm.

Example 3

A polymer composite having a polymer membrane formed on the base material upon photo-curing was obtained in the same manner as described in Example 1, except that the solids concentration of the photosensitive resin composition A used in Example I was changed from 5 wt. % to 3 wt. %. The film thickness obtained before photo-curing was 0.25 µm.

Example 4

A polymer composite having a polymer membrane, which was formed on the base material upon photo-curing and which had a hole pattern formed on the surface, was obtained in the same manner as described in Example 1, except that during exposure to light in Example 1, the product was exposed through a mask so that a pattern having many holes of 100 µm in diameter arranged would be obtained.

Example 5

A polymer composite having a polymer membrane, which was formed on the base material upon photo-curing and which had a hole pattern formed on the surface, was obtained in the same manner as described in Example 2, except that during exposure to light in Example 2, the product was exposed through a mask so that a pattern having many holes of 100 µm in diameter arranged would be obtained.

Example 6

A polymer composite having a polymer membrane, which was formed on the base material upon photo-curing and which had a hole pattern formed on the surface, was obtained in the same manner as described in Example 3, except that during exposure to light in Example 3, the product was exposed through a mask so that a pattern having many holes of 100 µm in diameter arranged would be obtained.

Example 7

A polymer composite having a polymer membrane, which was formed on the base material upon photo-curing and which had a 100 µm/200 µm line/space pattern formed on the surface, was obtained in the same manner as described in Example 1, except that during exposure to light in Example 1, the product was exposed through a mask so that a 100 µm/200 µm line/space pattern would be obtained.

Example 8

An aminosilane-coated slide glass (a product of MATSUNAMI GLASS IND.; hereinafter referred to as "APS-coated glass") was used as a base material having amino groups on the surface. Photosensitive resin composition A (solids concentration: 5 wt. %) was added dropwise onto the APS-coated glass, then formed into a film by spin coating (1000 rpm×30 seconds), dried for 10 minutes at 60° C., and then cooled to room temperature. The film thickness obtained was 0.90 µm. The resulting product was exposed to light, throughout its surface, by a high pressure mercury lamp (amount of exposure: 30 mJ/cm$^2$). Then, the exposed product was washed for 1 minute in water at 25° C., and then dried for 10 minutes at 60° C. As a result, a polymer composite, which had a polymer membrane formed on the base material upon photo-curing, was obtained.

Example 9

A polymer composite having a polymer membrane, which was forme on the base material upon photo-curing and which had a hole pattern formed on the surface, was obtained in the same manner as described in Example 8, except that during exposure to light in Example 8, the product was exposed through a mask so that a pattern having many holes of 100 µm in diameter arranged would be obtained.

Example 10

A poly-L-lysine-coated 96-well polystyrene plate (a product of Sumitomo Bakelite, trademark "SUMILON CELLTIGHT PL Plate 96F", 0.32 cm$^2$/well, hereinafter referred to as "PLL-coated resin plate") was used as a base material having amino groups on the surface. Photosensitive resin composition A (solids concentration: 1 wt. %) was added dropwise in an amount of 25 µl onto the PLL-coated resin plate, and then dried for 2 hours at 40° C. to form a film. Then, the product was exposed to light, throughout its surface, by a high pressure mercury lamp (amount of exposure: 200 mJ/cm$^2$). As a result, a polymer composite, which had a polymer membrane formed on the base material upon photo-curing, was obtained.

Example 11

A polymer composite having a polymer membrane formed on the base material upon photo-curing was obtained in the same manner as described in Example 1, except that photosensitive resin composition B (solids concentration: 5 wt. %) prepared by diluting a polyvinyl acetate saponification product, which incorporated 0.75 mol % of photosensitive compound 1 being a photosensitive compound having azido groups, with water/methanol=70/30 (wt. ratio) was used in place of the photosensitive resin composition A used in Example 1. The film thickness obtained before photo-curing was 1.0 µm.

Example 12

A polymer composite having a polymer membrane formed on the base material upon photo-curing was obtained in the same manner as described in Example 1, except that photosensitive resin composition C,(solids concentration: 5 wt. %) prepared by diluting a polyvinyl acetate saponification product, which incorporated photosensitive compound 3 being a photosensitive compound having azido groups, with water was used instead of the photosensitive resin composition A used in Example 1. The film thickness obtained before photo-curing was 1.0 µm.

Example 13

Photosensitive resin composition D (a product of Toyo Gosei Co., Ltd.; trademark "RTP-1001") was prepared by diluting a polyvinyl acetate saponification product, which incorporated 1.1 mol % of photosensitive compound 4 being a photosensitive compound having azido groups, with water. The photosensitive resin composition D (solids concentration: 5 wt. %) was added dropwise onto PLL-coated glass, then formed into a film by spin coating (1000 rpm×30 seconds), dried for 10 minutes at 60° C., and then cooled to room temperature. The film thickness obtained was 0.92 µm. This product was exposed to light, throughout its surface, by a high pressure mercury lamp (amount of exposure: 30 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Example 14

A polymer composite having a polymer membrane, which was formed on the base material upon photo-curing and which had a hole pattern formed on the surface, was obtained in the same manner as described in Example 13, except that during exposure to light in Example 13, the product was exposed through a mask so that a pattern having many holes of 100 µm in diameter arranged would be obtained.

Example 15

An aqueous solution containing photosensitive compound 5 having azido groups as a photo-crosslinking agent, and poly(meth)acrylamide-diaceton(meth)acrylamide copolymer at a ratio of 1:9 (weight ratio) (the aqueous solution was designated as photosensitive resin composition E) (a product of Toyo Gosei Co., Ltd.; trademark "PAD235") was prepared. The photosensitive resin composition E (solids concentration: 5 wt. %) was added dropwise onto PLL-coated glass, then formed into a film by spin coating (1000 rpm×30 seconds), dried for 10 minutes at 60° C., and then cooled to room temperature. The film thickness obtained was 1.98 μm. This product was exposed to light, throughout its surface, by a high pressure mercury lamp (amount of exposure: 45 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Example 16

A polymer composite having a polymer membrane, which was formed on the base material upon photo-curing and which had a hole pattern formed on the surface, was obtained in the same manner as described in Example 15, except that during exposure to light in Example 15, the product was exposed through a mask so that a pattern having many holes of 100 μm in diameter arranged would be obtained.

Example 17

An aqueous solution containing photosensitive compound 5 having azido groups as a photo-crosslinking agent, and polyvinyl pyrrolidone at a ratio of 1:9 (weight ratio) (the aqueous solution was designated as photosensitive resin composition F) (a product of Toyo Gosei Co., Ltd.; trademark "PVP-18") was prepared. The photosensitive resin composition F (solids concentration: 5 wt. %) was added dropwise onto PLL-coated glass, then formed into a film by spin coating (1000 rpm×30 seconds), dried for 10 minutes at 60° C., and then cooled to room temperature. The film thickness obtained was 0.58 μm. This product was exposed to light, throughout its surface, by a high pressure mercury lamp (amount of exposure: 45 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Example 18

A polymer composite having a polymer membrane, which was formed on the base material upon photo-curing and which had a hole pattern formed on the surface, was obtained in the same manner as described in Example 17, except that during exposure to light in Example 17, the product was exposed through a mask so that a pattern having many holes of 100 μm in diameter arranged would be obtained.

Example 19

An aqueous solution containing sodium bichromate (a product of Wako Pure Chemical Industries) as a photo-crosslinking agent, and polyvinyl acetate saponification product (a product of Nippon Synthetic Chemical Industry Co., Ltd., trademark "EG-30") at a ratio of 5:95 (weight ratio) (the aqueous solution was designated as photosensitive resin composition G) was prepared. The photosensitive resin composition G (solids concentration: 6 wt. %) was added dropwise onto PLL-coated glass, then formed into a film by spin coating (1000 rpm×30 seconds), dried for 3 minutes at 40° C., and then cooled to room temperature. The film thickness obtained was 0.81 μm. This product was exposed to light, throughout its surface, by a high pressure mercury lamp (amount of exposure: 60 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Example 20

A polymer composite having a polymer membrane, which was formed on the base material upon photo-curing and which had a hole pattern formed on the surface, was obtained in the same manner as described in Example 19, except that during exposure to light in Example 19, the product was exposed through a mask so that a pattern in an arrangement of many holes of 100 μm in diameter would be obtained.

Comparative Example 1

Soda lime slide glass (a product of Matsunami Glass Ind.,Ltd.;

hereinafter referred to as "non-coated glass") was used as a base material having no amino groups on the surface. Photosensitive resin composition A (solids concentration: 5 wt. %) was added dropwise onto the non-coated glass, then formed into a film by spin coating (1000 rpm×30 seconds), dried for 10 minutes at 60° C., and then cooled to room temperature. The film thickness obtained was 0.80 μm. This product was exposed to light, throughout its surface, by a high pressure mercury lamp (amount of exposure: 30 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Comparative Example 2

A polymer composite having a polymer membrane formed on the base material upon photo-curing was obtained in the same manner as described in Comparative Example 1, except that the conditions for spin coating used in Comparative Example 1 were changed from 1000 rpm×30 seconds to 2500 rpm×30 seconds. The film thickness obtained before photo-curing was 0.45 μm.

Comparative Example 3

A polymer composite having a polymer membrane formed on the base material upon photo-curing was obtained in the same manner as described in Comparative Example 1, except that the solids concentration of the photosensitive resin composition A used in Comparative Example 1 was changed from 5 wt. % to 3 wt. %. The film thickness obtained before photo-curing was 0.16 μm.

Comparative Example 4

A polymer composite having a polymer membrane, which was formed on the base material upon photo-curing and which had a hole pattern formed on the surface, was obtained in the same manner as described in Comparative Example 1, except that during exposure to light in Comparative Example 1, the product was exposed through a mask so that a pattern having many holes of 100 µm in diameter arranged would be obtained.

Comparative Example 5

A polymer composite having a polymer membrane, which was formed on the base material upon photo-curing and which had a hole pattern formed on the surface, was obtained in the same manner as described in Comparative Example 2, except that during exposure to light in Comparative Example 2, the product was exposed through a mask so that a pattern having many holes of 100 µm in diameter arranged would be obtained.

Comparative Example 6

A polymer composite having a polymer membrane, which was formed on the base material upon photo-curing and which had a hole pattern formed on the surface, was obtained in the same manner as described in Comparative Example 3, except that during exposure to light in Comparative Example 3, the product was exposed through a mask so that a pattern having many holes of 100 µm in diameter arranged would be obtained.

Comparative Example 7

A polymer composite having a polymer membrane, which was formed on the base material upon photo-curing and which had a line/space pattern formed on the surface, was obtained in the same manner as described in Comparative Example 1, except that during exposure to light in Comparative Example 1, the product was exposed through a mask so that a 100 µm/200 µm line/space pattern would be obtained.

Comparative Example 8

A 96-well polystyrene plate (a product of Sumitomo Bakelite Co. Ltd., trademark "SUMILON MULTIPLATE 96F", 0.32 cm$^2$/well, hereinafter referred to as "non-coated resin plate") was used as a base material having no amino groups on the surface. Photosensitive resin composition A (solids concentration: 1 wt. %) was added dropwise in an amount of 25 µl onto the non-coated resin plate, and then dried for 2 hours at 40° C. to form a film. Then, the product was exposed to light, throughout its surface, by a high pressure mercury lamp (amount of exposure: 200 mJ/cm$^2$). As a result, a polymer composite, which had a polymer membrane formed on the base material upon photo-curing, was obtained.

Comparative Example 9

The non-coated glass was used as a base material having no amino groups on the surface. Photosensitive resin composition B (solids concentration: 5 wt. %) was added dropwise onto the non-coated glass, then formed into a film by spin coating (1000 rpm×30 seconds), dried for 10 minutes at 60° C., and then cooled to room temperature. The film thickness obtained was 1.0 µm. This product was exposed to light, throughout its surface, by a high pressure mercury lamp (amount of exposure: 30 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Comparative Example 10

The non-coated glass was used as a base material having no amino groups on the surface. Photosensitive resin composition C (solids concentration: 5 wt. %) was added dropwise onto the non-coated glass, then formed into a film by spin coating (1000 rpm×30 seconds), dried for 10 minutes at 60° C., and then cooled to room temperature. The film thickness obtained was 1.0 µm. This product was exposed to light, throughout its surface, by a high pressure mercury lamp (amount of exposure: 30 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Comparative Example 11

The non-coated glass was used as a base material having no amino groups on the surface. Photosensitive resin composition D (solids concentration: 5 wt. %) was added dropwise onto the non-coated glass, then formed into a film by spin coating (1000 rpm×30 seconds), dried for 10 minutes at 60° C., and then cooled to room temperature. The film thickness obtained was 0.91 µm. This product was exposed to light, throughout its surface, by a high pressure mercury lamp (amount of exposure: 30 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Comparative Example 12

A polymer composite having a polymer membrane, which was formed on the base material upon photo-curing and which had a hole pattern formed on the surface, was obtained in the same manner as described in Comparative Example 11, except that during exposure to light in Comparative Example 11, the product was exposed through a mask so that a pattern having many holes of 100 µm in diameter arranged would be obtained.

Comparative Example 13

The non-coated glass was used as a base material having no amino groups on the surface. Photosensitive resin composition E (solids concentration: 5 wt. %) was added dropwise onto the non-coated glass, then formed into a film by spin coating (1000 rpm×30 seconds), dried for 10 minutes at 60° C., and then cooled to room temperature. The film thickness obtained was 1.82 µm. This product was exposed to light, throughout its surface, by a high pressure mercury lamp (amount of exposure: 45 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Comparative Example 14

A polymer composite having a polymer membrane, which was formed on the base material upon photo-curing and which had a hole pattern formed on the surface, was obtained in the same manner as described in Comparative Example 13, except that during exposure to light in Comparative Example 13, the product was exposed through a mask so that a pattern having many holes of 100 μm in diameter arranged would be obtained.

Comparative Example 15

The non-coated glass was used as a base material having no amino groups on the surface. Photosensitive resin composition F (solids concentration: 5 wt. %) was added dropwise onto the non-coated glass, then formed into a film by spin coating (1000 rpm×30 seconds), dried for 10 minutes at 60° C., and then cooled to room temperature. The film thickness obtained was 0.58 μm. This product was exposed to light, throughout its surface, by a high pressure mercury lamp (amount of exposure: 45 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Comparative Example 16

A polymer composite having a polymer membrane, which was formed on the base material upon photo-curing and which had a hole pattern formed on the surface, was obtained in the same manner as described in Comparative Example 15, except that during exposure to light in Comparative Example 15, the product was exposed through a mask so that a pattern having many holes of 100 μm in diameter arranged would be obtained.

Comparative Example 17

The non-coated glass was used as a base material having no amino groups on the surface. Photosensitive resin composition G (solids concentration: 6 wt. %) was added dropwise onto the non-coated glass, then formed into a film by spin coating (1000 rpm×30 seconds), dried for 3 minutes at 40° C., and then cooled to room temperature. The film thickness obtained was 0.81 μm. This product was exposed to light, throughout its surface, by a high pressure mercury lamp (amount of exposure: 60 mJ/cm$^2$). Then, the exposed product was washed for 1 minute in water at 25° C., and then dried for 10 minutes at 60° C. As a result, a polymer composite having a polymer membrane formed on the base material upon photo-curing was obtained.

Comparative Example 18

A polymer composite having a polymer membrane, which was formed on the base material upon photo-curing and which had a hole pattern formed on the surface, was obtained in the same manner as described in Comparative Example 17, except that during exposure to light in Comparative Example 17, the product was exposed through a mask so that a pattern having many holes of 100 μm in diameter arranged would be obtained.

Example 21

Ashing Treatment

The polymer composite having the hole pattern, prepared in Example 4, was irradiated with $O_2$ plasma (300 W, 20 seconds) for ashing. As a result, the film thickness of the exposed areas decreased by 0.3 μm. After the ashing, the unexposed areas were irradiated with high energy electron rays, and the resulting gas was introduced into ICP-MS. Peaks ascribed to organic components were not detected, and it was confirmed that traces of the photosensitive resin composition on the surface of the base material in the unexposed areas were removed.

Test Example 1

Test for Exposure to Water-Based Solvent

Each of the polymer composites obtained in Examples 1 to 21 and Comparative Examples 1 to 18 was dipped in water or various water-based solvents at 37° C. After lapse of 3 days and 10 days, each of the polymer composites was observed to evaluate the stability of the polymer composites in water or the various water-based solvents. The solvents used were pure water, an aqueous solution of potassium dihydrogenphosphate and disodium hydrogenphosphate (phosphate buffer solution, pH 7.4), a 10% aqueous solution of acetone, a 5% aqueous solution of sodium dodecyl sulfate, and a 10% fetal bovine serum-containing Dulbecco modified Eagle's medium (a product of Nissui Pharmaceutical Co., Ltd.; Dulbecco's Modified Eagle's Medium). For the water and the phosphate buffer solution, dipping tests at 60° C. were also conducted, and each of the polymer composites after 3 days and 10 days was observed. In connection with the polymer composites of Example 4 and Comparative Example 4 dipped in the 10% fetal bovine serum-containing Dulbecco modified Eagle's medium at 37° C., the statuses of these polymer composites before and after dipping are shown in FIG. 1A to 1F by way of example.

In all the tests, the polymer composites of Examples 1 to 21 after dipping showed no changes in surface shape as compared with those before dipping. They were in stable states without peeling or collapse of the polymer membrane due to swelling. The polymer composites of Comparative Examples 1 to 18, on the other hand, were in states in which the polymer membrane did not settle on, but peeled off, the base material, or the polymer membrane did not completely peel off, but was so swollen as to partly rise from the base material, in all the tests conducted.

These findings confirmed that the polymer composite of the present invention, which has the polymer membrane formed on the base material having the surface modified with amino groups, could maintain its structure stably in water or a water-based solvent.

Test Example 2

Cell Pattern Culture Test

The polymer composite obtained in Example 21 was used as a base material for cell culture, and a cell pattern culture test was conducted. The base material was sterilized in an autoclave, and then bovine vascular endothelial cells were incubated thereon for 10 days. A 10% fetal bovine serum-containing Dulbecco modified Eagle's medium was used.

Figure 2:
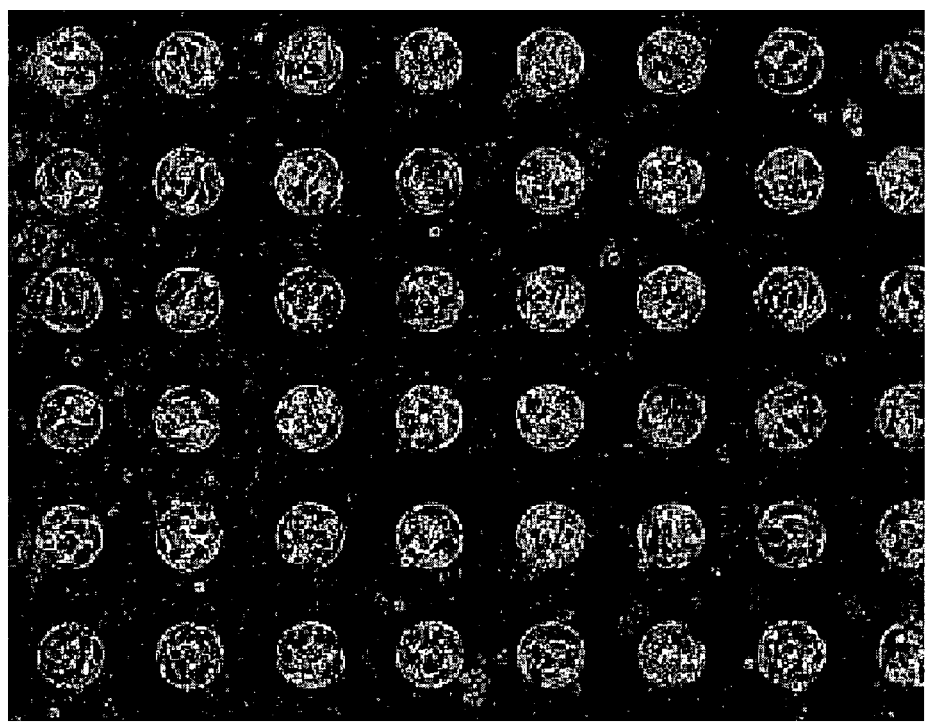
FIG. 2 is a view showing an example of the state of culture during pattern cell culture evaluation.

During incubation, the polymer composite maintained its structure stably in the culture medium. The cells did not adhere onto the water-soluble polymer membrane, but adhered only to the site where the glass was exposed to the outside. FIG. 2 shows the status at 24 hours after start of incubation during evaluation of cell pattern culture.

The above-described embodiments illustrate the polymer composite of the present invention. However, the present invention is not limited to these embodiments, and can be changed and modified variously. It should be understood that such changes, substitutions and alterations can be made therein without departing from the spirit and scope of the invention as defined by the appended claims.

What is claimed is:

1. A polymer composite comprising a base material and a polymer membrane provided on at least a part of said base material, said polymer membrane having at least hydrophilicity, said polymer composite being used in a state exposed to water or a water-based solvent.
    wherein said base material per se has amino groups exposed at a surface thereof, and
    said polymer membrane is a resin film formed by photo-crosslinking a photosensitive resin composition consisting essentially of a water-soluble polymer having azido groups as photosensitive groups,
    wherein when the amino groups present on the surface of the base material and photosensitive groups present in said photosensitive resin composition are irradiated with light, some of the amino groups and some of the photosensitive groups undergo a chemical reaction to form a covalent bond, and wherein said resin film is fixed to said base material by said covalent bond.

2. The polymer composite according to claim 1, wherein said resin film is formed by exposing to light an entire surface of said photosensitive resin composition coated on said base material to crosslink said photosensitive resin composition.

3. The polymer composite according to claim 1, wherein said resin film is provided on said part of said base material by pattern exposure and development of said photosensitive resin composition coated on said base material to remove unexposed areas.

4. The polymer composite according to claim 3, wherein after said development, traces of said photosensitive resin composition on said surface of said base material in said unexposed areas are removed.

5. The polymer composite according to claim 4, wherein said amino groups on said surface of said base material in said unexposed areas are removed.

6. The polymer composite according to claim 1, wherein said photosensitive groups have a structure of the following formula (1) or formula (2):

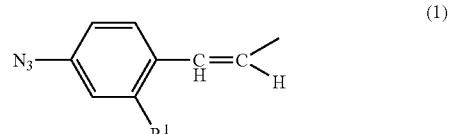

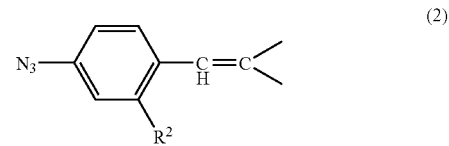

where $R^1$ and $R^2$ each represent a hydrogen atom, a sulfonic group, or a sulfonate group.

7. The polymer composite according to claim 1, wherein said water-based solvent is at least one member selected from the group consisting of a physiological buffer solution, a protein-containing aqueous solution, a DNA-containing aqueous solution, an RNA-containing aqueous solution, a sugar-containing aqueous solution, a liquid culture medium, and a cell suspension.

8. The polymer composite according to claim 1, wherein said polymer composite is a matrix material for a biosensor, or a base material for cell culture.

9. The polymer composite according to claim 1, wherein the photosensitive resin composition is a solution of the water-soluble polymer in water.

* * * * *